(12) United States Patent
Kalser et al.

(10) Patent No.: US 10,660,688 B2
(45) Date of Patent: May 26, 2020

(54) CRYOTHERAPY DEVICE WITH CRYOPROTECTION AND METHODS FOR PERFORMING CRYOTHERAPY WITH CRYOPROTECTION

(71) Applicants: Gary Kalser, Winter Park, FL (US); Gregory L. Mayback, Cooper City, FL (US)

(72) Inventors: Gary Kalser, Winter Park, FL (US); Gregory L. Mayback, Cooper City, FL (US)

( * ) Notice: Subject to any disclaimer, the term of this patent is extended or adjusted under 35 U.S.C. 154(b) by 732 days.

(21) Appl. No.: 14/709,060

(22) Filed: May 11, 2015

(65) Prior Publication Data

US 2015/0320473 A1 Nov. 12, 2015

Related U.S. Application Data

(60) Provisional application No. 61/991,953, filed on May 12, 2014.

(51) Int. Cl.
*A61B 18/02* (2006.01)
*A61B 18/00* (2006.01)
*A61B 90/00* (2016.01)

(52) U.S. Cl.
CPC .......... *A61B 18/02* (2013.01); *A61B 18/0218* (2013.01); *A61B 2018/00547* (2013.01);
(Continued)

(58) Field of Classification Search
CPC ................. A61B 18/02; A61B 18/0218; A61B 2018/00005; A61B 2018/00041; A61B 2018/00029; A61B 2018/0212; A61B 2018/00547; A61B 2018/0275; A61B 2018/0281; A61B 2018/0287; A61B 2018/00791; A61B 2018/00293; A61B 2018/00898; A61B 2018/0231; A61B 2018/0237; A61B 2018/0243;
(Continued)

(56) References Cited

U.S. PATENT DOCUMENTS 6,041,787 A * 3/2000 Rubinsky ................. A01N 1/02
128/898
7,494,802 B2 2/2009 Tseng et al.
(Continued)

OTHER PUBLICATIONS

SpaceOAR System; http://www.augmenix2.com; 2014 Augmenix dated Jun. 22, 2014.
(Continued)

*Primary Examiner* — Thomas A Giuliani
(74) *Attorney, Agent, or Firm* — Gregory L. Mayback; Dickinson Wright PLLC (57) ABSTRACT

A cryoprotective device includes a hollow cryoprotective probe having a distal tip, a removable obturator, and at least one integral temperature sensor monitoring temperature at least adjacent the distal tip. An injector is able to inject a cryoprotective substance (CPS) through the cryoprotective probe and out the distal tip when the obturator is removed. The CPS is of a material that prevents freezing of a substance at which it is injected when adjacent cryotherapy occurs. A processor monitors temperature of the at least one the temperature sensor and can indicate if a preset limit is exceeded.

6 Claims, 7 Drawing Sheets

(52) U.S. Cl.
CPC ............... *A61B 2018/00791* (2013.01); *A61B 2018/00898* (2013.01); *A61B 2018/0212* (2013.01); *A61B 2018/0293* (2013.01); *A61B 2090/0463* (2016.02)

(58) Field of Classification Search
CPC ...... A61B 2018/025; A61B 2018/0256; A61B 2018/0262; A61B 2018/0268; A61B 2017/00274; A61B 90/04; A61B 2090/0463; A01N 1/02; A01N 1/0221
USPC ...... 606/20–26; 607/96, 104, 105, 107, 113, 607/114
See application file for complete search history.

(56) References Cited

U.S. PATENT DOCUMENTS

| | | |
|---|---|---|
| 8,562,208 B2 | 10/2013 | Yeager et al. |
| 2003/0120267 A1 | 6/2003 | Kaufman et al. |
| 2007/0167776 A1* | 7/2007 | Kochavi .............. A61B 5/6885 600/439 |
| 2007/0224169 A1 | 9/2007 | Sliwa, Jr. et al. |
| 2012/0089211 A1* | 4/2012 | Curtis .................... A61B 18/02 607/105 |
| 2013/0184695 A1 | 7/2013 | Fourkas et al. |

OTHER PUBLICATIONS

SpaceOAR System; http://www.augmenix.com; 2014 Augmenix dated Jun. 22, 2014.
International Search Report and Written Opinion for International Application No. PCT/US2015/030242 dated Aug. 14, 2015.

* cited by examiner

CRYOTHERAPY DEVICE WITH CRYOPROTECTION AND METHODS FOR PERFORMING CRYOTHERAPY WITH CRYOPROTECTION

CROSS-REFERENCE TO RELATED APPLICATIONS

This application claims the priority, under 35 U.S.C. § 119, of U.S. Provisional Patent Application No. 61/991,953, filed May 12, 2014; the prior application is herewith incorporated by reference herein in its entirety.

STATEMENT REGARDING FEDERALLY SPONSORED RESEARCH OR DEVELOPMENT

Not Applicable

FIELD OF THE INVENTION

The present invention lies in the field of cryotherapy. The present disclosure relates to a cryotherapy device having cryoprotection and methods for performing cryotherapy with cryoprotection, for example, to treat prostate cancer and other diseases or conditions.

BACKGROUND OF THE INVENTION

Cryotherapy is a medical procedure used to treat a number of different diseases. It is also used to treat benign and malignant lesions. Cryotherapy is used in many of the human organs including liver, kidney, uterus, heart, eyes, breast, lung, kidney, and prostate. With regard to the various procedures in which cryotherapy is used, treatment of prostate cancer is one of the most common. Accordingly, this example for treatment of prostate cancer is utilized herein to describe and illustrate the disadvantages associated with use of cryotherapy, as well as the advantages of the instant invention, but the invention should not be considered as limited to this example.

Prostate cancer is the most common cancer diagnosis in men (except skin cancer). It is the second-most common cause of cancer deaths in men over the age of 65 (lung cancer is the most common). Current methods to treat prostate cancer include prostatectomy (robotic), radiation therapy, cryotherapy, and watchful waiting. Robotic prostatectomy and radiation are very expensive and cost between $40,000 and $60,000. They can have significant morbidity. Cryotherapy is the least expensive treatment, even less than watchful waiting. Cure rates are equivalent to radiation and slightly less than surgery.

One major complication of cryotherapy is injury to adjacent normal tissues. For example, in cryosurgery of the prostate used for treating cancer, the most significant side effect is injury to the nerves needed for erectile function. This detrimental side effect is extremely common because injury to these nerves occurs in 80% to 90% of the procedures performed today. The reason why this injury is so common is because these nerves are in close proximity to the prostate. Therefore, these nerves are directly exposed to lethal levels of cold temperature during cryotherapy, resulting in sexual dysfunction. Currently there is no device/method that significantly reduces this side effect.

Figure 1:
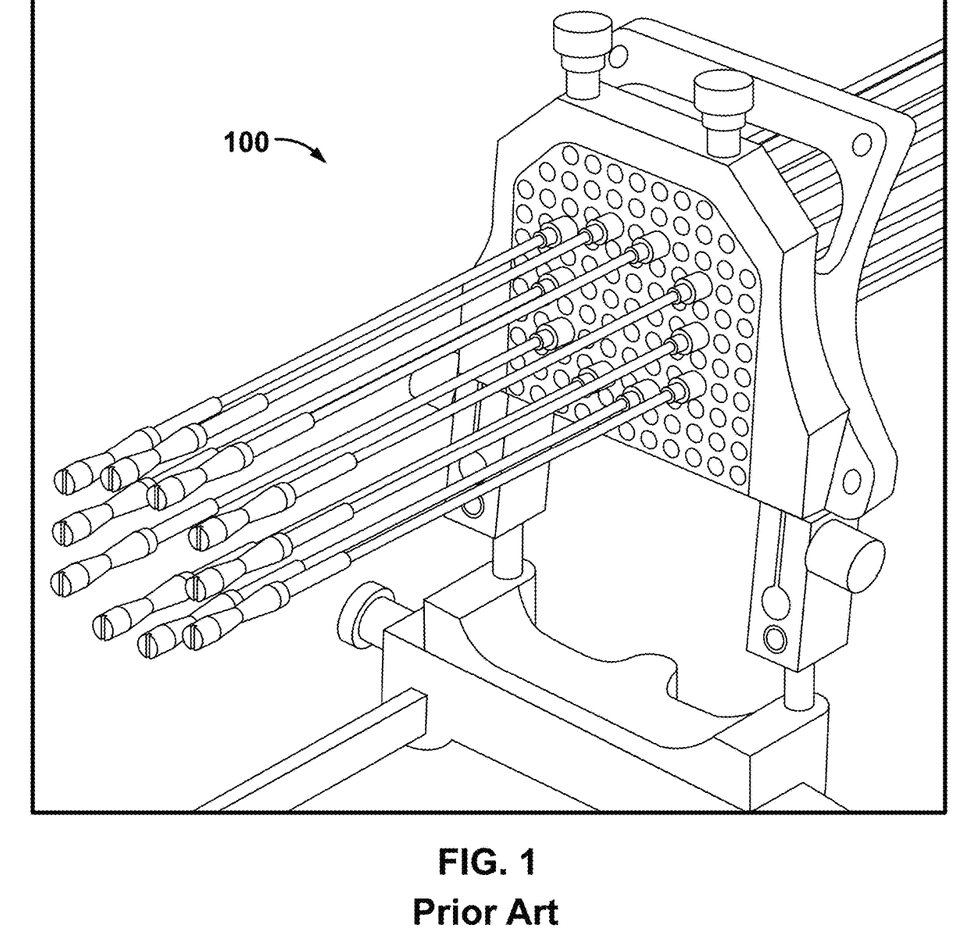
FIG. 1 is a photograph of a fragmentary, perspective view of a prior art cryotherapy needle template and cryotherapy needles from above a front side thereof.

In the example of a treatment for prostate cancer, cryotherapy devices insert hollow needles through the perineum, i.e., the region between the genitals and the anus. Liquid nitrogen or liquid argon is injected through the needles and is used to freeze the prostate itself, thereby eradicating the prostate cancer. Those of skill in the art know how cryotherapy treatment on the prostate is performed and one excellent exemplary overview of this procedure is found on the Web at https://www.youtube.com/watch?v=-OnqA-mJDWg&app=desktop, titled "Overview of Prostate Cryotherapy" by Galil Medical. A needle guide template having a row-and-column array of needle guide bores is placed against the perineum with the patient in the lithotomy position. With ultrasound visualization, the surgeon inserts cryoablation needles though various bores in the array and into the prostate. Temperature probes can also be inserted through other bores to monitor temperature within the prostate or adjacent, such as at the rectal wall or at the sphincter. Urethral protection is provided with devices such as a urethral warming catheter. Cycles of freezing are applied to the prostate under visualization until treatment has finished. The needles and template are removed after treatment is completed. An example of such a needle guide template 100 is shown in FIG. 1.

Present devices used to treat prostate cancer with cryotherapy are often used in salvage procedures where cancer has recurred or where other procedures (such as external beam radiation therapy or high dose rate brachytherapy) have failed. Now, cryotherapy is being used to treat primary prostate cancer, in which the entire prostate is treated along with the cancer. This procedure has beneficial results because it prevents the cancer from reoccurring in another location subsequently. Another procedure is becoming popularized—focal cryotherapy of the prostate. In this procedure, only a quadrant or section of the prostate that contains the cancer is treated. Focal cryotherapy was developed to eliminate erectile function injuries to help preserve erectile function, but it has succeeded only in exchange for an increase in the possibility of cancer reoccurrence. Focal cryotherapy is reserved for a select group of patients whose probability of cancer reoccurrence in another section of the prostate is minimal.

As mentioned above, one major side effect of any cryotherapy to treat the prostate (hindering it from becoming more popular) is the relatively high incidence of erectile dysfunction from nerve damage. Yet, another complication of prostate cryotherapy is rectal injury, which can and does occur because the posterior prostate is in close proximity to the rectum, e.g., in the Denonvilliers Fascia. The anterior rectum is at risk for thermal injury when adequately low temperatures for cell death in the posterior prostate occur. This risk is especially an issue when treating a post-radiated prostate because that space has been reduced from scarring.

In summary, current cryotherapy devices are not equipped to prevent nerve damage in a patient, thereby increasing the risk of impotence.

There are other ways to treat prostate cancer, for example. Surgical removal of the prostate, radical prostatectomy, is one way. However, radical prostatectomy is only effective if the prostate cancer is organ-confined. Side effects of radical prostatectomy surgery include temporary or permanent urinary incontinence and impotence. In addition, even if the patient is not impotent, removal of the prostate will result in dry orgasms for the patient. Further, there is a danger that the surgeon could cut one or more of the nerves, resulting in erectile dysfunction.

Radiation therapy is another form of treatment for prostate cancer. Forms of radiation therapy include permanent seed implants, high dose rate temporary brachytherapy, and external beam radiation therapy. One form of radiation therapy is the use of permanent seed implants. When using permanent seed implants therapy, radioactive seeds are injected into the prostate gland. The seeds are comprised of radioactive material encased within a titanium shell. A major disadvantage of seed implant therapy is the fact that it is difficult to determine whether cancer has spread during the procedure. In addition, side effects include bowel and bladder issues.

High-dose-rate brachytherapy is another treatment type and uses catheters that are inserted into the prostate and the tumor with the use of a CAT scan to position the catheters. An insertion device pushes a radioactive iridium wire into the catheters one by one to treat the tumor. Although high-dose-rate brachytherapy is seen as an effective alternative to permanent seed implants, the equipment and training costs associated with the treatment are very high. In addition, there is a distinct possibility that the seeds migrate and, in doing so, ultimately deliver too much radiation, causing damage to non-cancerous tissues, or deliver too little radiation, thereby failing to give a lethal dose to the cancer.

A final treatment type is external beam radiation therapy, which is used typically in situations where cancer has spread and is not confined to the prostate. Typical side effects include bowel and bladder issues because the radiation affects healthy tissue.

Each of these forms of treatment has the ability to burn normal adjacent tissue in a random and uncontrollable way. While cryotherapy is growing in its use for many procedures, especially for treatment of prostate cancer, currently, there is no feasible way to prevent these types of injuries to adjacent nerves/normal tissue without compromising the cancer-removing operation. One attempt to do so was through use of helium-warming probes, but that attempt was unsuccessful for a variety of reasons.

Thus, a need exists to overcome the problems with the prior art systems, designs, and processes as discussed above.

Rapid transition polymers (RTP) are discussed herein and it is believed that a brief overview would be beneficial. RTP developed by Pluromed, Inc., are polymers that exist in a liquid state at low temperatures and at room temperature, but quickly transition to a gel at body temperature. This phase change is fully reversible by cooling. It is noted that the polymers cannot re-solidify once dissolved. Some RTP are able to be injected into a mammal. One RTP substance was developed as an endovascular occlusion gel for vascular surgery under Pluromed's trademark LeGoo® and is FDA approved. In such use, LeGoo® is a viscous liquid at room temperature and becomes a firm plug in the vessel in which it is injected at body temperature. Once used in such a vessel-occluding procedure, a cooling mechanism, such as sterile ice, is applied to the site of the gelled RTP or cold saline is injected intravascularly until blood flow in the occluded vessel is restored. This RTP polymer is also FDA approved for the use in endoscopic urologic surgery to prevent proximal stone migration under Pluromed's trademark BackStop®. In particular, injected BackStop® forms a plug in the ureter to prevent stone migration during lithotripsy. BackStop® is marketed by Boston Scientific.

SUMMARY OF THE INVENTION

The invention provides cryoprotection systems and methods for performing cryotherapy with cryoprotection that overcome the hereinafore-mentioned disadvantages of the heretofore-known devices and methods of this general type and that provide such features with the ability to protect nerves and other healthy tissue at the surgical site that might be damaged by exposure to the cryotherapy cold.

In particular, the cryotherapy devices and methods for performing cryotherapy with cryoprotection that are described herein utilize materials (such as rapid transition polymers) having thermal protective properties in ways not previously known or described. In particular, the above-described RTP has a freezing point well below zero degrees Centigrade. Thus, this RTP can be used as insulation to protect vital tissues (including nerves) from excessive cold during cryotherapy procedures. As used herein, the term RTP is defined as set forth above but other substances that shield one tissue from another adjacent tissue with protection from cold temperatures caused by cryotherapy are envisioned as equally applicable to the presently described inventive systems and methods.

The set of materials that provide cryoprotection as used herein is referred to as a cryoprotective substance or "CPS". Accordingly, if "RTP" is used in a particular exemplary embodiment hereinbelow, any CPS can be substituted for the RTP and used similarly and, in so describing this, such alternative materials are to be considered as in addition to or instead of a described single one of the cryoprotective materials, such as the RTP.

In addition to RTP, other CPS that are available and likewise have cryoprotective properties are referred to in the art as AminoFix® and EpiFix®. These products comprise processed dehydrated amniotic tissue allograft membranes and are used to deliver essential growth factors and cytokines. The latter two proteins are used to promote healing and to prevent inflammation and scarring. These products are used for a variety of reconstructive surgical procedures. However, another property of these materials that was not heretofore known is that a dehydrated property of these cells is able to provide cryoprotection. While it is known that dehydrated cells are more tolerant to cold than are normal hydrated cells, they have not been heretofore used for protection of adjacent tissues during cryotherapy procedures. Although AminoFix® and EpiFix® are marketed to be used in many different areas of the body it has never been mentioned for its cryoprotective properties but such properties exist and this material can be used instead of or in addition to any of the other materials described herein for protecting adjacent tissues from cryotherapy injury. The process for using dehydrated cells such as AminoFix® and EpiFix® for the purpose of cryoprotection is exactly the same as the process previously described for using RTP for cryoprotection. This is because, for example, AminoFix® and EpiFix® both come in an FDA-approved injectable form. This injectable form is used for orthopedic diseases and use of the dehydrated cells (not growth factors et al.) for cryoprotective purposes was not discovered until the inventors discovered the instant cryoprotective systems and processes. As such, the scope of the inventive systems and methods include any use of a dehydrated cell for cryoprotective purposes.

Yet another CPS is made by Augmenix, Inc., which created a compound called SpaceOAR®. This compound is a substance used to prevent radiation injury to the rectum. It utilizes ethylene glycol to create a space, thereby preventing damage to the rectum during external radiation beam therapy. In addition, Augmenix, Inc., also manufactures a product called TraceIT®, which is used to radiographically mark soft tissue during a surgical procedure. This compound includes a radiopaque polyethylene glycol hydrogel. The inventors have discovered that these compounds can be used in the inventive systems and methods to protect tissue from thermal injury.

There are several mechanisms by which the CPS can yield thermal protection. First, in the example of RTP, when injected into the body in its liquid state, the RTP liquid creates a space by its presence to establish a protective boundary around targeted tissue as it transitions from a liquid to a gel. This space protects the sensitive tissue not only because it increases the distance between the sensitive cellular structure and the adjacent target of the freezing, but it also has "antifreeze" properties that prevent the protected tissue from cooling to a point where the cellular structure crystallizes. The active ingredient in the RTP known in the art as LeGoo® Endovascular Occlusion Gel that gives LeGoo® its antifreeze properties is ethylene glycol. This molecule has unique cryoprotective properties not previously described for use in the medical field. The scope of the inventions described herein include not only LeGoo® but also any RTP or other substance that includes ethylene glycol. The systems and methods also include use of ethylene glycol (or equivalent materials or compounds) that are both biologically safe and have antifreeze properties or where such a product is linked or bonded to another substance that makes the product biologically safe when used for its antifreeze properties.

The cryoprotective methods described herein are applicable to any surgical procedure where cryotherapy is desirable and adjacent tissues needing protection are present. Cryotherapy has been used in almost every organ in the body. Examples include, but are not limited to, procedures involving the skin, the eye, the esophagus, the stomach, the liver, the rectum, the pancreas, the heart, the nervous system, and bones. In each of these examples, there are risks and complications associated with injury to adjacent vital structures and, therefore, the inventive cryoprotective systems and methods are equally applicable to such different procedures even where they are not described in detail herein. In particular, even though the description herein goes into detail for removing cancer in a prostate, it is not limited thereto. Prostate cancer treatment is merely one exemplary use. Thus, the described systems and methods provide a mechanism by which standard cryotherapy provides the cooling and the CPS form a better and safer insulator than air, saline, or any other material.

Accordingly, in the example of cryotherapy to remove cancer in a prostate, injection of the polymer/substance between the prostate and the erectile nerves increases the space therebetween. In addition to physical separation, the polymer/substance's antifreeze properties serve to prevent adjacent cooling from penetrating into the protected tissue (surrounding the prostate and including the vascular and nerve structures) to an extent that would be sufficient to crystallize and, thereby, destroy that protected tissue. In particular, when the freezing of the target tissue does comes into contact with the CPS, it is thermally protected and, in the example of RTP, the gel liquifies from its outer perimeter inwards, surrounding the tissue/nerves located inside the gel with "liquid antifreeze" and, thus, protects the tissue/nerves. This antifreeze property of RTP protects cell membranes within the gel by preventing the membrane from fracturing, which occurs when cells are subjected to crystallization. As such, use of CPS such as RTP in cryotherapy prostate surgery forms an inventive system and method that prevents erectile nerve damage and rectal injuries.

One example use of cryotherapy in the heart is to treat cardiac arrhythmias. The typical procedure involves placing a balloon in the pulmonary artery. This balloon is used to freeze and kill adjacent aberrant nerves that are responsible for the arrhythmias. A serious complication of this procedure is damage to the phrenic nerve. If such an injury happens, the diaphragm no longer is able to contract and the patient is never able to breathe normally again. As such, injecting the CPS (e.g., RTP) between the phrenic nerve and the pulmonary artery protects the phrenic nerve during this form of treatment as described herein with respect to the other alternative embodiments of use.

Yet another example how the CPS can be used is in treatment of tumors and lesions around the eye and the eye orbit. There are many vital structures that can be in close proximity to a targeted lesion in the eye, such as the retina, the lacrimal duct, and the optic nerve. By injecting the CPS (e.g., RTP) between the lesion and the vital structure, a protective layer is formed and protects that vital structure from cryotherapy that is performed on the lesion. Then, cryotherapy treatment of the tumor/lesion can occur with confidence because of the protection that CPS provides to the tissue adjacent to that tissue being treated with cryotherapy.

Yet another use for cryotherapy is in the gastrointestinal tract. Examples of such uses include the treatment of Barrett's esophagus as well as tumors and cancers in the esophagus. A serious and life-threatening complication of cryotherapy in the esophagus is perforation. Another possible complication is stricture formation. By placing the CPS (e.g., RTP) between the layers of muscles and mucosa before cryotherapy begins, injuries to the adjacent tissues from the cryotherapy can be prevented. In a similar fashion, cryotherapy is used to treat gastric antral ectasia and gastric tumors. Again, the CPS (e.g., RTP) is placed between the targeted lesions and the different layers on the intestinal wall to prevent perforation that could be caused by cryotherapy.

Yet another example of cryotherapy use is in the treatment of pancreatic diseases. These include the treatment of pancreatitis and pancreatic tumors. It is known that the pancreas is very difficult to reach surgically. Therefore, many endoscopic procedures are being developed using cryotherapy. It is known that serious complications can occur if the patient's bile duct is injured but, using the inventive CPS between the bile duct and the targeted lesion, bile duct injuries are prevented.

Yet another example of the use of cryotherapy is for pain control. Certain nerves can be responsible for causing severe pain. An example of such a disease is trigeminal neuralgia. Accordingly, ablation of the nerves causing the pain can result in elimination of the pain. But, such ablation can and does cause injury to the adjacent tissues. Thus, the CPS (e.g., RTP) can be injected around the nerve to prevent collateral injury on non-targeted adjacent nerves and vessels.

Yet another common use of cryotherapy is in the treatment of cutaneous lesions. Certain areas of the body such as the hand and feet are at particular risk for vascular injury due to their lack of collateral circulation. Vascular necrosis of digits has been described to occur following these types of procedures. Vascular necrosis can be prevented with the inventive systems and processes by injecting the CPS (e.g., RTP) around the targeted lesion prior to carrying out cryotherapy.

Yet another use of cryotherapy is in the treatment of rectal proctitis, which is most commonly caused by radiation. In this procedure, the CPS (e.g., RTP) is injected underneath the lesion to prevent perforation and fistula formation when cryotherapy occurs.

The examples described above are not to be considered as limiting the possible uses of the inventive systems and methods with placement of the CPS to protect ancillary injury caused previously by cryotherapy. One skilled in the art, therefore, knows to which procedures the inventive systems and methods can be extended.

Different methods of cryotherapy exist and depend upon the manufacturer of the cryotherapy equipment. This cryoprotective methods and systems described herein involve pretreatment with the CPS to protect tissue that is not desired to receive the cryotherapy treatment (i.e., it is not intended to be destroyed with cold and, instead, is to be protected). The CPS is injected to protect the tissue before cryotherapy needles/probes are inserted and, therefore, which cryotherapy device available in the marketplace that is used for the surgery becomes irrelevant.

As detailed herein, one very good exemplary use of the inventive systems and methods involve protection of nerves surrounding the prostate. Before describing those systems and methods, various aspects of prostate cryotherapy are described with regard to FIGS. 1 to 8.

Figure 2:
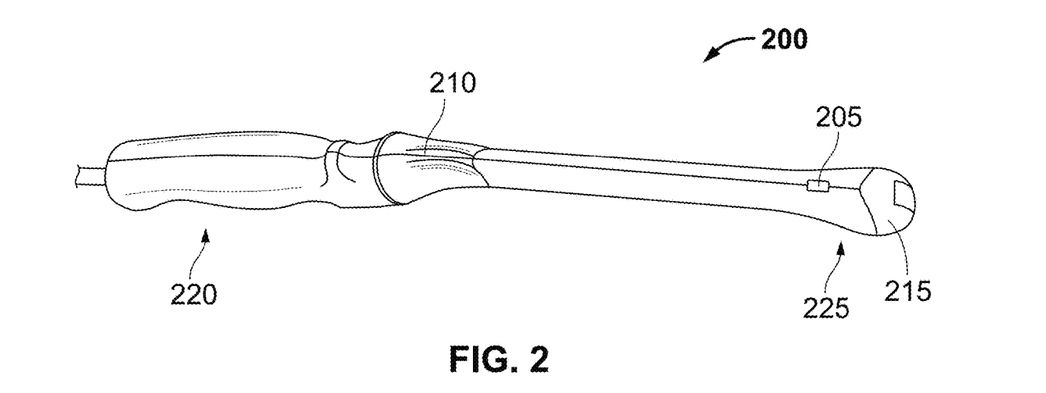
FIG. 2 is a photograph of a fragmentary, perspective view of a prior art ultrasonic probe from above a top side thereof.

FIG. 2 illustrates a transducer guide or ultrasonic probe 200 that is manufactured by Micro Convex. The probe 200 has a proximal end 220 and a distal end 225. The proximal end 220 of the probe 200 is a handle for gripping by a user during a procedure. The distal end 225 of the probe 200 has an acoustic lens 215. The probe 200 also includes a groove 210 and an opening 205 that are both used to secure an attachment 400 shown in FIG. 4.

An ultrasonic generating portion of the probe 200 includes a transducer, a backing material, an acoustic matching layer, and an acoustic lens, e.g., lens 215. The transducer or piezoelectric element (not shown) is used to generate ultrasonic waves. A voltage is applied to electrodes that are attached to both sides of the transducer. The transducer oscillates by expanding and contracting, which, at ultrasonic frequencies, generates an ultrasonic sound wave. A backing material (not shown) is located behind, i.e., in a proximal location from, the transducer and is used to prevent excessive vibration. An acoustic matching layer (not shown) is used to reduce reflection of the ultrasonic waves. The acoustic lens 215 is used to focus the ultrasonic waves to improve resolution.

Figure 3:
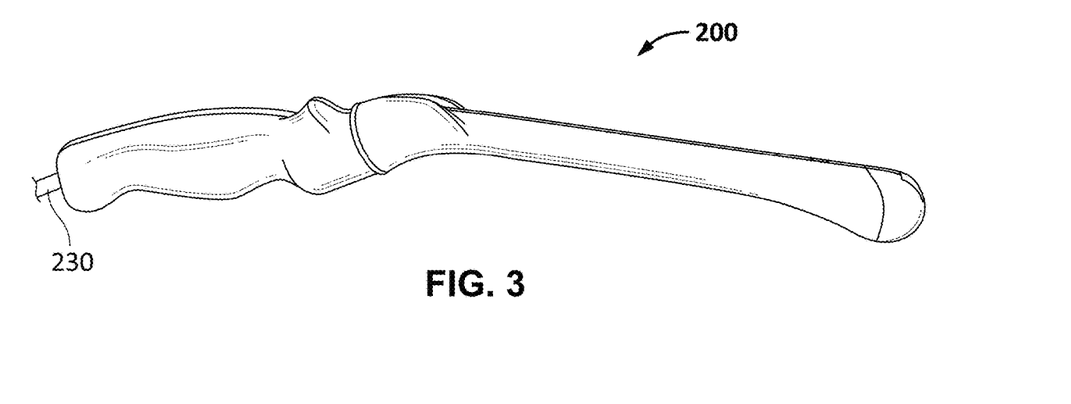
FIG. 3 is a photograph of a fragmentary, perspective view of the ultrasonic probe of FIG. 1 from above a right side thereof.

FIG. 3 illustrates another view of probe 200. This view shows a cord 230 for connection to an ultrasound platform. The ultrasound platform (not shown) is used to acquire, present, and analyze data obtained from the probe 200.

Figure 4:
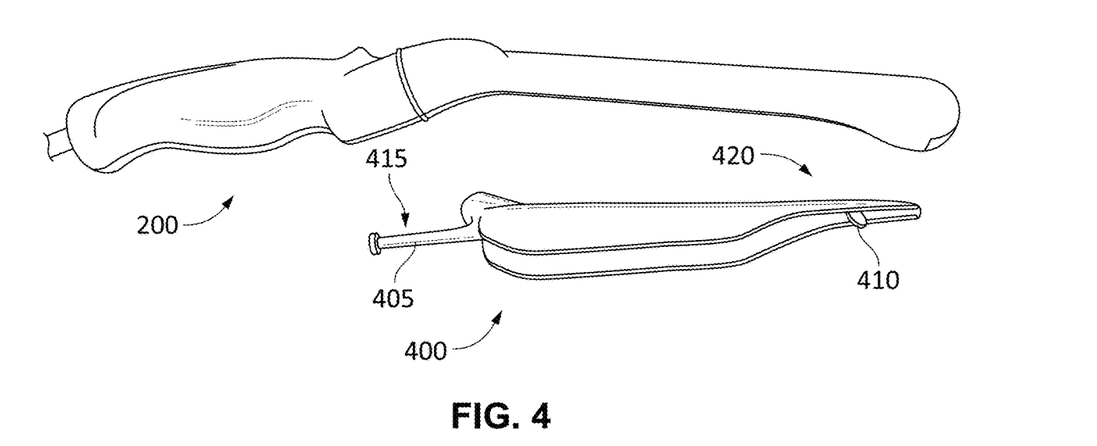
FIG. 4 is a photograph of a fragmentary, perspective view of the ultrasonic probe of FIG. 1 and a probe attachment from below a right side thereof.
Figure 5:
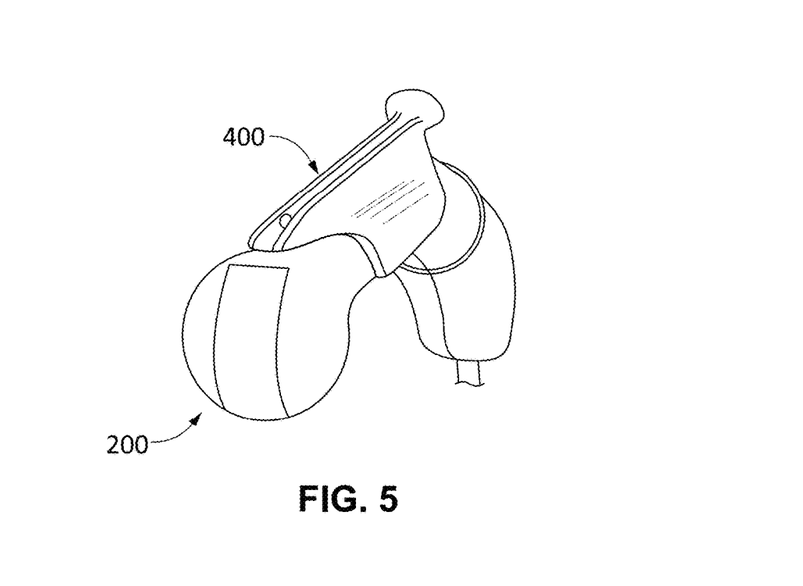
FIG. 5 is a photograph of a fragmentary, perspective view of the attachment and probe of FIG. 4 in an attached configuration from above a distal end thereof.
Figure 6:
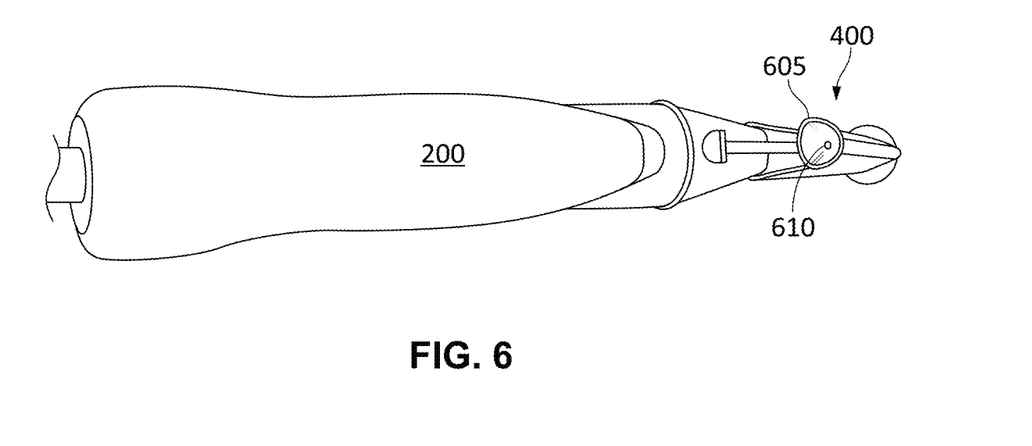
FIG. 6 is a photograph of a fragmentary, perspective view of the attachment and ultrasonic probe of FIG. 5 from above a proximal end thereof.

FIG. 4 illustrates the attachment 400 for the probe 200. The attachment 400 includes an extension 405 on a proximal end 415 thereof. The extension 405 fits into the groove 210 on the probe 200. The attachment 400 also includes a protrusion 410 for placement into the opening 205 of probe 200. FIG. 5 shows the probe 200 connected to attachment 400. FIG. 6 illustrates a proximal side of the attachment 400 when it is connected to the probe 200. A funnel shaped opening 605 on the proximal end of the attachment 400 leads to a channel 610 that runs longitudinally from the proximal end 415 to the distal end 420 of the attachment 400. The opening 605 and the channel 610 are used to insert and guide surgical portions of the prior art cryotherapy device.

Figure 7:
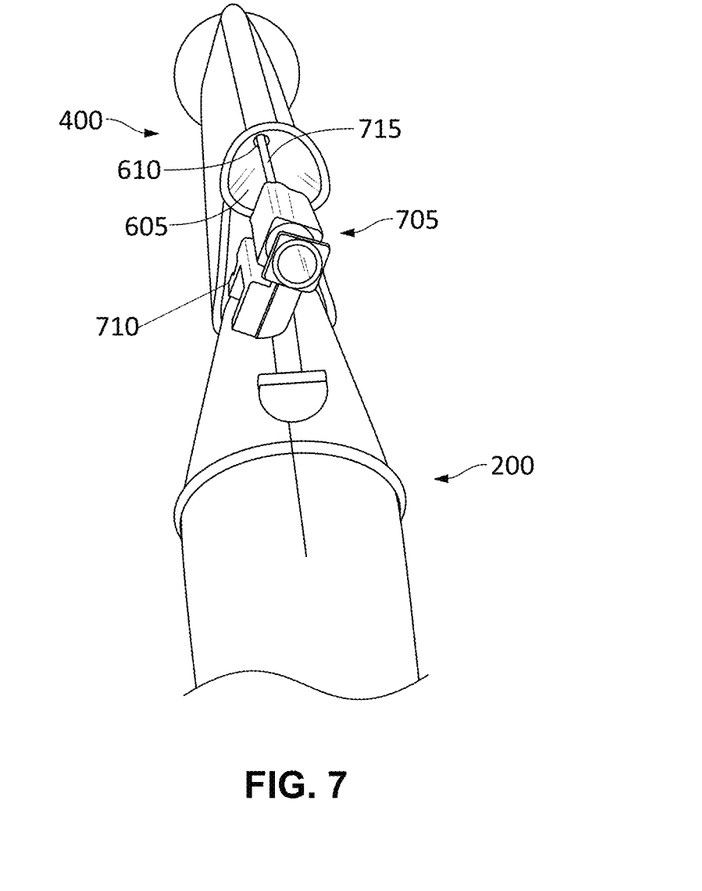
FIG. 7 is a photograph of a fragmentary, perspective view of the attachment and ultrasonic probe of FIG. 5 from above a proximal end thereof with a needle catheter inserted through a guide of the attachment.
Figure 8:
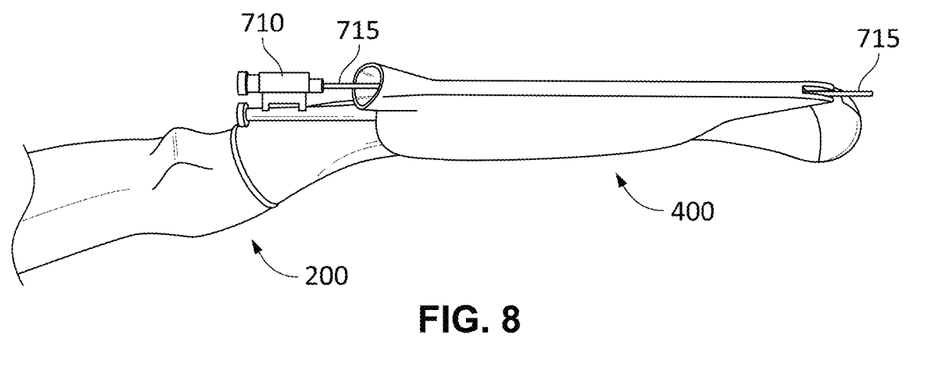
FIG. 8 is a photograph of a fragmentary, perspective view of the attachment and probe of FIG. 7 from above a right side thereof.
Figure 9:
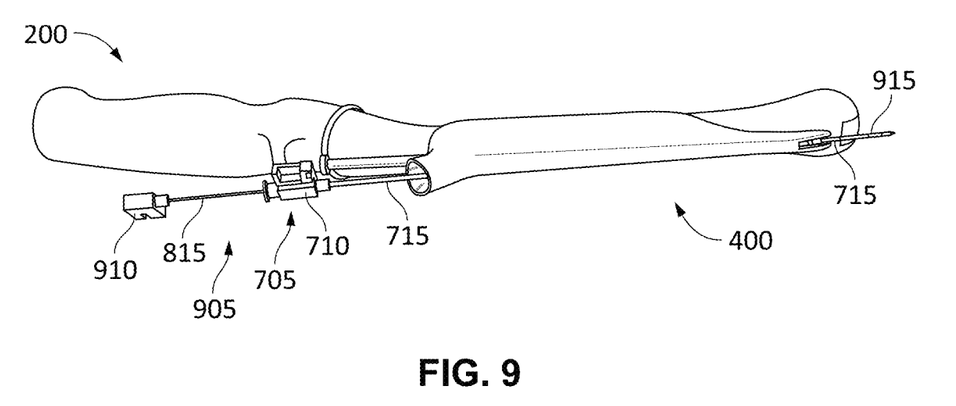
FIG. 9 is a photograph of a fragmentary, perspective view of the attachment and probe of FIG. 8 with a cryotherapy needle inserted into the needle catheter from above a left side thereof.

FIGS. 7, 8, and 9 show other views of the probe 200 and the attachment 400. In these views, a cryotherapy catheter 705 is shown. This exemplary catheter 705 includes a luer connector 710 and a needle guide 715. In the views of FIGS. 7 to 9, the needle guide 715 has been placed into the funnel 605 and passes entirely through the channel 610 to exit the other end. In such a position, when the distal end 225 of the probe 200 has been inserted into the anus of the patient, the channel 610 is positioned at a spot for positioning a cryotherapy injection needle 905 to pierce tissue and approach the prostate and its surrounding areas. The cryotherapy injection needle 905 can also be referred to as a cryotherapy probe.

FIG. 9 shows an example of a cryotherapy injection needle 905 used with the catheter 705 and the attachment 400. The cryotherapy injection needle 905 includes a proximal connector 910 and a hollow needle shaft 915. In use, the needle shaft 915 is inserted into a proximal end of the catheter 705 through the connector 710 and, thereby, through the channel 610 of the attachment 400. In this way, when the channel 610 is aligned with the surgical site, the needle shaft 915 can be pushed through the catheter 705 and into the patient for administering the cryotherapy treatment.

During a standard cryotherapy procedure, a temperature probe is placed wherever the surgeon desires to monitor temperature of tissue. In particular, during prostate surgery, the surgeon needs to monitor the temperature of the neuro-vascular tissues. This is because any damage to the neuro-vascular tissues (caused by the tissue/nerves receiving cold) can cause erectile dysfunction of the penis, which is to be avoided. The temperature probe is inserted through the connector 400 and is left at the prostatic plexis during prostate cryotherapy. Accordingly, the surgeon slides the connector 400 back away from the installed temperature probe (not illustrated) and then uses a cryotherapy connector 400 with the probe 200 to locate the prostate and perform the cryotherapy. In particular, the ultra-thin cryotherapy injection needle 905 is inserted into the prostate gland using an incision in the perineum, e.g., in an area between the anus and the scrotum. Visualization of the surgery occurs with the ultrasound probe 200 and with telemetry from the temperature sensor at the neuro-vascular tissues. The sensor and/or the probe 200 can include a processor that receives signals from the sensor/probe and provides information, such as temperature, to the surgeon using the systems and methods. The surgeon uses the information from the ultrasound probe 200 to find and destroy the prostatic tissue and monitors the temperature probe or the information provided by the processor to make sure the neuro-vascular tissues remains at a pre-defined safe temperature.

With the foregoing and other objects in view, there is provided, a method for preventing damage to adjacent tissue at a surgical site including the steps of locating the tissue to be protected, placing a cryoprotective device at least one of at and adjacent the tissue to be protected, injecting a cryoprotective substance (CPS) through the cryoprotective device at least one of at and adjacent the tissue, at least one of positioning a temperature sensor at least one of at and adjacent the CPS and positioning a temperature sensor at least one of at and adjacent the tissue, monitoring a temperature of at least one of the CPS and the tissue with the temperature sensor, and carrying out cryotherapy at the surgical site without harm to the tissue.

With the objects in view, there is also provided a cryoprotective device, comprising a hollow cryoprotective probe having a distal tip, a removable obturator, and at least one integral temperature sensor monitoring temperature at least adjacent the distal tip, an injector injecting a cryoprotective substance (CPS) through the cryoprotective probe and out the distal tip when the obturator is removed, the CPS preventing freezing of a substance at which it is injected when adjacent cryotherapy occurs, and a processor monitoring temperature of the at least one the temperature sensor.

In accordance with another feature, the CPS comprises a rapid transition polymer.

In accordance with a further feature, the CPS comprises an anesthetic.

In accordance with an added feature, the CPS comprises dehydrated cells.

In accordance with an additional feature, the dehydrated cells comprise dehydrated amniotic tissue allograft membranes.

In accordance with yet another feature, the locating, placing, injecting, positioning and monitoring steps are repeated for each area of different tissues to be protected.

In accordance with yet a further feature, further CPS is injected through the cryoprotective device if a preset temperature limit is exceeded.

In accordance with a concomitant feature, the processor notifies a user if the temperature monitored by the temperature sensor exceeds a preset temperature limit.

Although the invention is illustrated and described herein as embodied in a cryotherapy device and methods for performing cryotherapy with thermal protection, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. Although the invention is illustrated and described herein as embodied in a cryotherapy device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which.

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

It will be appreciated that embodiments of the systems and methods described herein may be comprised of one or more conventional processors and unique stored program instructions that control the one or more processors to implement, in conjunction with certain non-processor circuits and other elements, some, most, or all of the functions of the powered injector devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system. A "program," "software," "application," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 10:
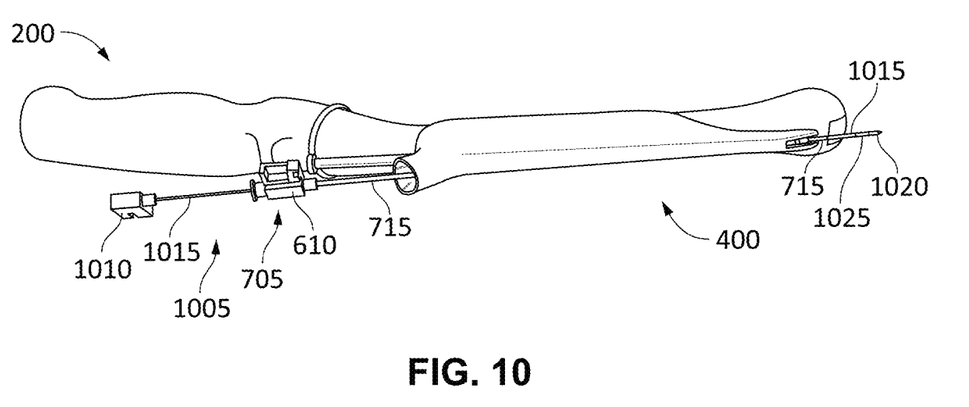
FIG. 10 is a photograph of a fragmentary, perspective view of a cryotherapy pretreatment device in accordance with an exemplary embodiment.

Described now are exemplary embodiments of the present invention. Referring now to the figures of the drawings in detail and first, particularly to FIG. 10, there is provided a cryotherapy pretreatment device 1005. Like FIG. 9, FIG. 10 shows the ultrasonic probe 200, the attachment 400, and the cryotherapy catheter 705. In contrast to the cryotherapy injection needle 905, however, is the presence of the cryotherapy pretreatment device 1005, which is inserted through the catheter 705 before cryotherapy begins. It is noted that, the probe 200 and attachment 400 is only one exemplary use of the cryoprotective systems and methods described herein and these systems and methods can uses any ultrasonic visualization device and associated cryotherapy aligning device (such as the template 100), and, in addition, provide the cryotherapy pretreatment device 1005.

The cryotherapy pretreatment device 1005 includes a proximal connector 1010 and a hollow needle shaft 1015 that terminates in a distal tip 1020. In use, the needle shaft 1015 is inserted into a proximal end of the catheter 705 through the connector 710 and, thereby, through the channel 610 of the attachment 400. In this way, when the channel 610 is aligned with the surgical site, the needle shaft 1015 can be pushed through the catheter 705 and into the patient for administering the cryotherapy pretreatment.

Figure 11:
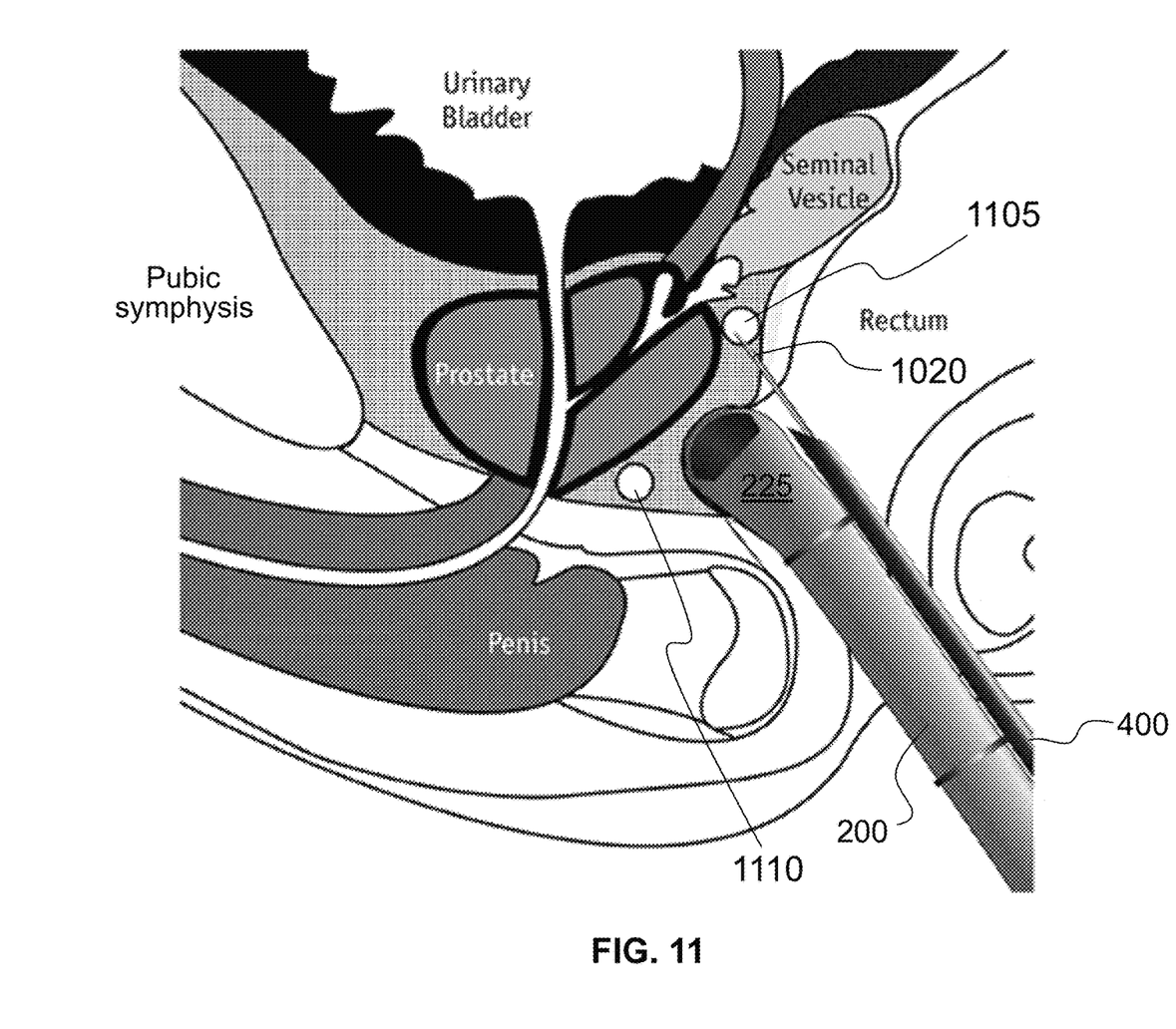
FIG. 11 is a sagittal, cross-sectional view through a cryotherapy treatment area of a prostate and with the probe of FIG. 2 inserted in the anus for ultrasonic visualization of the treatment area.
Figure 12:
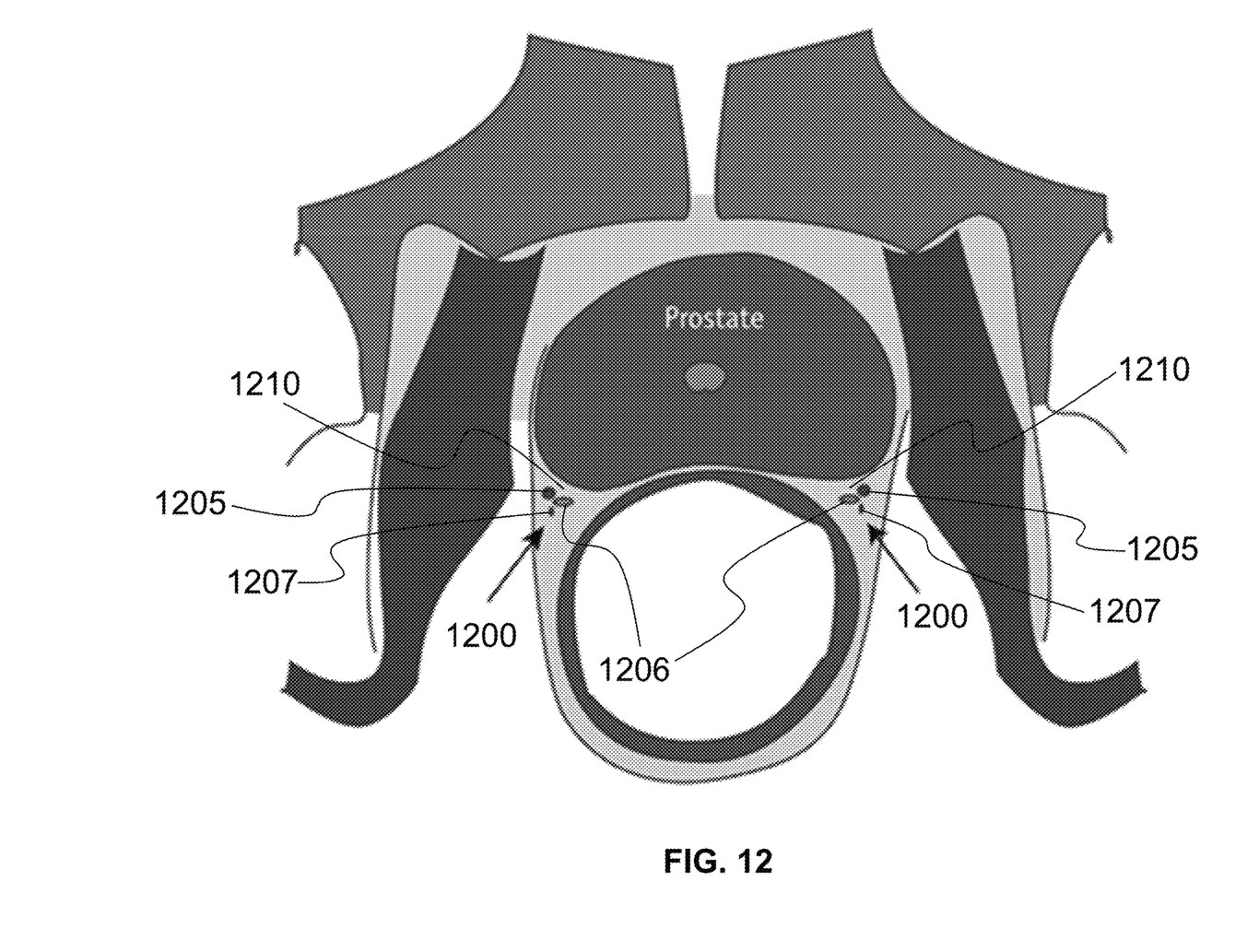
FIG. 12 is a transverse, cross-sectional view through the cryotherapy treatment area of FIG. 11.

In particular regard to administering cryotherapy to a prostate, the distal end 225 of the probe 200 is placed through the anus and adjacent the prostate as shown in FIG. 11. With use of the probe 200 (e.g., with doppler ultrasound), the neuro-vascular bundle and/or the nerves of the prostatic plexus adjacent the prostate are located; these structures are close to or adjacent the seminal vesicle. In particular, the bundle 1200 including the arteries 1205, the veins 1206, and the nerves 1207 are shown in FIG. 12 on both the left and right sides of the prostate.

The distal tip 1020 of the cryotherapy pretreatment device 1005 is guided trans-rectally alongside the nerves (bilaterally) up to and adjacent the prostatic plexus with an obturator therein to protect the CPS injection channel. When placed adjacent the prostatic plexus as shown in FIG. 11, the obturator is removed and the CPS 1105 is injected through the proximal connector 1010 under visualization through the cryotherapy pretreatment device 1005 to form a liquid space surrounding the entirety of the prostatic plexus or at least the side of the prostatic plexus facing the prostate. Ideally, both the left and right sides are injected with the CPS 1105 at the locations shown in FIG. 12 and identified with numeral 1210. As the CPS 1105 fills up the space at locations 1210, the bundle 1200 is both moved away from the prostate and protected from cryotherapy to be performed on the prostate with the antifreezing properties of the CPS 1105. If desired, the CPS 1105 can also be injected at other areas surrounding the prostate, such as area 1110 shown in FIG. 11.

The cryotherapy pretreatment device 1005 also has an integral temperature sensor 1025 adjacent the distal tip 1020. In an exemplary embodiment, the integral temperature sensor 1025 can be a single temperature sensor or a set of spaced apart independent temperature sensors (not illustrated) located and extending away from the distal tip 1020. In such a configuration, when pretreatment using CPS is finished, the cryotherapy pretreatment device 1005 can be left at the prostatic plexus to place the temperature sensor near the prostatic plexus and monitor temperature at and/or near the CPS protective space. One exemplary embodiment of a cryotherapy pretreatment device 1005 with an integral temperature sensor 1025 has the temperature sensor as a fiberoptic sensor(s) having a hollow injection channel with a distal injection port. The sensor(s) is(are) used to determine temperature of the area around the prostatic plexus during the cryotherapy procedure. During the cryotherapy procedure, the freeze ball will penetrate through the capsule of the prostate and then encounter the CPS 1105. Because the CPS 1105 surrounds the nerves 1207 (as well as the vessels 1205, 1206), these structures will be protected and preserved. Additionally, because the cryotherapy pretreatment device 1005 has an integral injection channel, any sensing of lowered temperature beyond a pre-set floor can be counteracted by manually or automatically placing more CPS 1105 in the target area.

At the termination of the procedure, the cryotherapy pretreatment device 1005 is removed, its temperature monitor/sensor having insured that the targeted tissue (e.g., nerves) have not been exposed to temperature that would crystallize the respective tissue.

In an exemplary embodiment, the cryotherapy pretreatment device 1005 is approximately 6 mm or 18-French.

There are several different methods of injecting the CPS 1105. For example, the CPS 1105 can be injected using a standard transrectal doppler ultrasound probe with a guidance apparatus attached to the probe. The transrectal doppler ultrasound probe with the guidance apparatus is placed in the rectum prior to initiating the cryosurgery. The neuro-vascular bundle 1200 is identified at its usual location, which is at the apex of the prostate on both the right and left side of the prostate. An injection needle, usually 22 gauge, is placed through the guidance apparatus. Then the injection needle is guided to the space 1210 between the neuro-vascular bundle 1200 and the prostate. The CPS 1105 is injected through the needle, thus creating a protective space between the neuro-vascular bundle 1200 and the prostate. This process is performed on both the right and left sides of the prostate. Afterwards, the cryosurgical procedure can be initiated in the usual fashion.

Alternatively, the cryosurgical procedure can be initiated first. In this exemplary method, a cryogrid (e.g., template 100) is attached to a stabilizing device. The grid has holes that are used to stabilize both the cryoprobes and the temperature sensors. The cryogrid has both an X axis (letters) and a Y axis (numbers), which gives every hole a specific coordinate. The exact coordinates of the locations of both the cryoprobes and the temperature sensors will vary from patient to patient depending on the specific three-dimensional geometry of the prostate. A transrectal doppler probe is placed in the rectum and attached to the same stabilizing unit. The neuro-vascular bundles 1200 are identified using doppler. A 20-gauge needle is placed through one of the holes in the grid and is directed to the neuro-vascular bundles 1200 on one side of the prostate. The CPS 1105 is injected in the space 1210 between the neuro-vascular bundle 1200 and the prostate. If a temperature sensor is provided at the distal end thereof, the needle is left in a position to monitor the temperature of the CPS 1105 or adjacent the neuro-vascular bundle 1200. This process is repeated for the neuro-vascular bundle 1200 on the other side of the prostate. Likewise, the CPS 1105 can also be injected at space between the rectum and the prostate (Denonvilliers Fascia). The latter will provide protection of the rectum from thermal injury.

By having a probe that contains both an injection port for the CPS and thermal sensors alongside the neuro-vascular bundles and the prostate, as well as in the space between the rectum and the prostate, the operating surgeon has the advantage of knowing the temperature of these critical spaces during cryotherapy, as well as having the ability to inject more CPS if the temperature of any becomes too low or if the space becomes too small. This probe also can be repositioned if necessary without affecting the surgical procedure. In an exemplary embodiment where the probe is provided with multiple temperature sensors, the probe will have the unique ability to measure the temperatures at multiple critical locations (e.g., in the CPS and outside the CPS) in order to prevent injury along the entire length of the neuro-vascular bundle and/or the rectum. After this cryo-protection is performed, standard cryoprobes are placed through the grid at the appropriate coordinates to completely ablate the entire prostate or just the cancerous lesions (focal therapy).

At the termination of the procedure, all of the probes are removed and discarded. Doppler ultrasound is then used to document the integrity of the neuro-vascular bundles by measuring blood flow.

Figure 13:
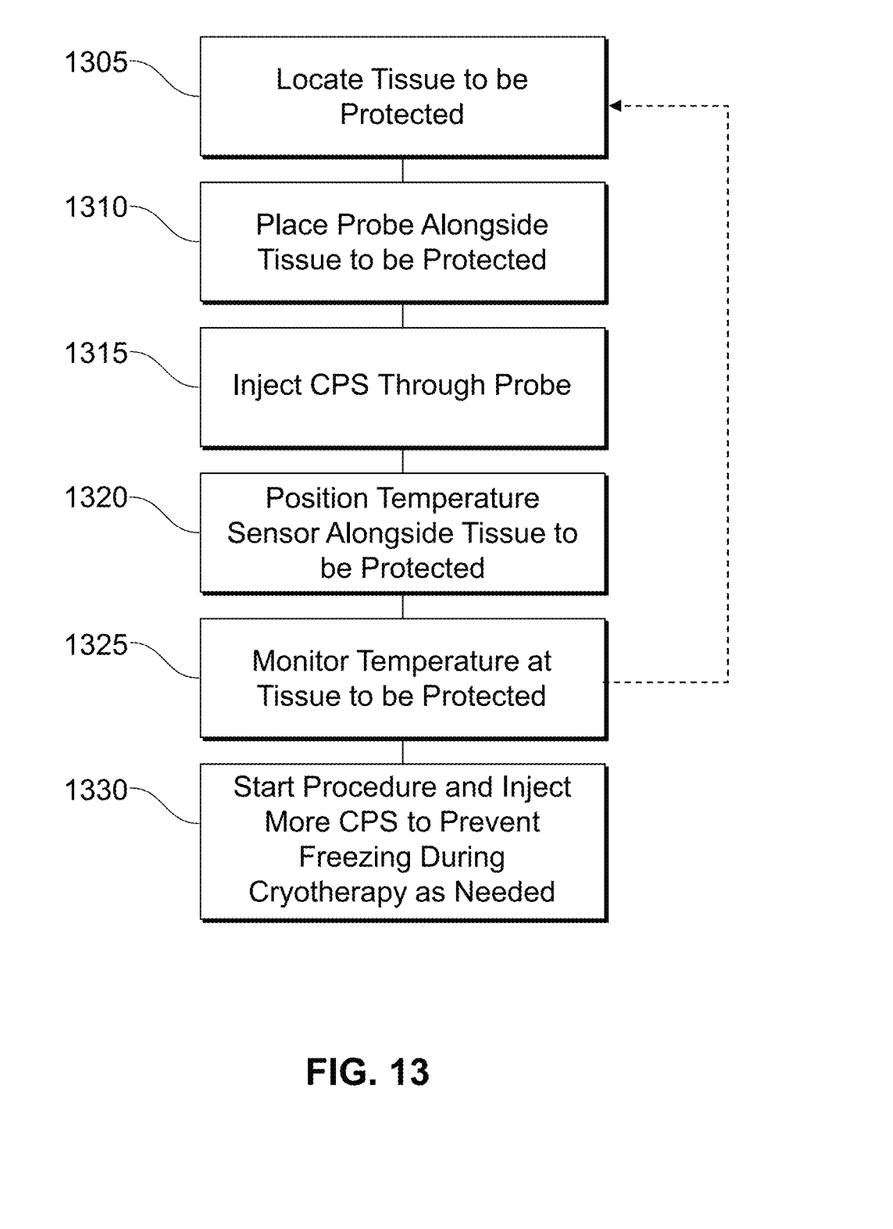
FIG. 13 is a block diagram of a method for protecting nerves during a cryotherapy procedure.

FIG. 13 is a block diagram of using the inventive systems and methods to prevent the freezing of nerves in a neuro-vascular bundle (e.g., prostatic plexus) during the removal of cancerous cells from a prostate using cryotherapy. At block 1305, the neuro-vascular bundle near the prostate is located. In one exemplary embodiment, the neuro-vascular bundle(s) is(are) located using doppler ultrasound. At block 1310, once the neuro-vascular bundle(s) has(have) been found, the cryotherapy pretreatment device 1005 is placed trans-rectally alongside each neuro-vascular bundle and, in particular, the cryotherapy pretreatment device 1005 is placed alongside the nerves bilaterally.

At block 1315, the CPS is injected through the cryotherapy pretreatment device 1005. The CPS (e.g., RTP or saline) can be initially placed through the cryotherapy pretreatment device 1005 and alongside the nerves after an obturator is removed from the needle. In an exemplary embodiment, the CPS can comprise RTP, an anesthetic, and/or dehydrated cells such as dehydrated amniotic tissue allograft membranes.

At block 1320, the cryotherapy pretreatment device 1005 positions the temperature sensor adjacent the bundle protected by the CPS. In an exemplary embodiment, the temperature sensor is a fiber optic sensor. It is noted that such temperature sensors are valuable but are not required for use of the instant systems and methods for cryotherapy protection.

At block 1325, a temperature of the area near the neuro-vascular bundle is monitored using the sensor.

Steps 1305 to 1320 are repeated (indicated with dashed line) for each area of tissue to be protected, which can include multiple sites at a particular area of tissue.

At block 1330, cryotherapy begins and, if a preset temperature limit is exceeded, then further CPS is injected to prevent freezing. During the cryotherapy procedure, a freeze ball produced by the procedure will penetrate through the capsule of the prostate and encounter the CPS. If the CPS is RTP, the RTP gel will liquefy and insulate the protected space from the damaging cold. Due to the unique properties of the ethylene glycol and the additional space created by injecting the RTP around the nerves, these structures are preserved and are not damaged by the adjacent cryotherapy procedure. Similar protection is provided by other forms of CPS as described herein. The inventive probe is removed once the cryotherapy procedure is terminated.

In an alternative embodiment where the cryotherapy pretreatment device 1005 has a separate fiber optic sensor as the temperature sensor, then, at block 1320, a catheter is threaded through the cryotherapy pretreatment device 1005 to lay alongside the neuro-vascular bundle.

Another exemplary embodiment of a method for protecting tissue during cryotherapy includes placement of a bi-planer trans-rectal doppler probe in a properly prepared rectum. Using doppler ultrasound the nerves are identified by locating the neuro-vascular bundles in both the sagital and transverse planes. The CPS is prepared pursuant to the manufacturer's instructions, if any. The cryotherapy pretreatment device 1005 (e.g., a 6-French needle) is placed through a guidance apparatus. The cryotherapy pretreatment device 1005 is guided to the/each neuro-vascular bundle using doppler ultrasound. If RTP is the CPS, then approximately 5 cc of the RTP is injected alongside the neuro-vascular bundle. This injection is repeated on the contralateral side. The cryotherapy pretreatment device 1005 is retracted and repositioned in a space between the prostate and the rectum (Denonvilliers Fascia) if desired and approximately 5 cc of the RTP is injected into this space as well. The doppler ultrasound probe is removed and the cryosurgical procedure is initiated in the typical fashion. If desired, one or more cryotherapy pretreatment devices 1005 have the integral temperature probes placed adjacent or in tissue desiring to be protected and the temperature of those tissues are monitored during the cryotherapy procedure. Upon termination of the cryosurgical procedure, the neuro-vascular bundles are rescanned to document acceptable blood flow and, therefore, identify lack of injury.

Even though RTP has been described herein as the measures by which insulation and physical protection of targeted tissue occurs, saline, which could also contain an anesthetic, can be infused alternatively and/or additionally during the protective procedure.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The phrase "at least one of A and B" is used herein and/or in the following claims, where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A cryoprotective device, comprising:
   a hollow cryoprotective needle probe shaped to pierce human tissue and having:
     a distal tip;
     a removable obturator; and
     at least one integral temperature sensor monitoring temperature of the tissue that is adjacent the distal tip when the distal tip has pierced the tissue and at least temporarily resides within the tissue;
   an injector injecting a cryoprotective substance (CPS) through the cryoprotective probe and out the distal tip into the tissue when the distal tip is within the tissue and the obturator is removed, the CPS preventing freezing of the tissue in which it is injected when adjacent cryotherapy occurs; and
   a processor monitoring temperature detected by the at least one temperature sensor.

2. The device according to claim 1, wherein the CPS comprises a rapid transition polymer.

3. The device according to claim 1, wherein the CPS comprises an anesthetic.

4. The device according to claim 1, wherein the CPS comprises dehydrated cells.

5. The device according to claim 4, wherein the dehydrated cells comprise dehydrated amniotic tissue allograft membranes.

6. The device according to claim 1, wherein the processor notifies a user if the temperature monitored by the temperature sensor exceeds a preset temperature limit.

* * * * *